US009877900B2

(12) United States Patent
Doucet et al.

(10) Patent No.: US 9,877,900 B2
(45) Date of Patent: Jan. 30, 2018

(54) USE OF COSMETICS AGAINST INFRARED RADIATION

(75) Inventors: Olivier Doucet, Roquebrune Cap Martin (FR); Muriel Pujos, Nice (FR); Cécile Robert, Nice (FR); Dorothée Bernini, Monaco (MC); Marc Pissavini, Nice (FR)

(73) Assignee: Coty Germany GmbH, Mainz (DE)

( * ) Notice: Subject to any disclaimer, the term of this patent is extended or adjusted under 35 U.S.C. 154(b) by 0 days.

(21) Appl. No.: 14/232,729

(22) PCT Filed: Jul. 13, 2012

(86) PCT No.: PCT/EP2012/063839
§ 371 (c)(1),
(2), (4) Date: Feb. 13, 2014

(87) PCT Pub. No.: WO2013/007829
PCT Pub. Date: Jan. 17, 2013

(65) Prior Publication Data
US 2014/0154191 A1 Jun. 5, 2014

(30) Foreign Application Priority Data

Jul. 14, 2011 (EP) .................................. 11173973

(51) Int. Cl.
| | |
|---|---|
| *A61L 15/44* | (2006.01) |
| *A61L 15/20* | (2006.01) |
| *C07C 69/67* | (2006.01) |
| *C07C 69/73* | (2006.01) |
| *C07H 3/02* | (2006.01) |
| *C07C 69/40* | (2006.01) |
| *C07C 43/178* | (2006.01) |
| *A61K 8/19* | (2006.01) |
| *A61K 8/26* | (2006.01) |
| *A61K 8/29* | (2006.01) |
| *A61K 8/67* | (2006.01) |
| *A61K 8/97* | (2017.01) |
| *A61Q 17/04* | (2006.01) |

(52) U.S. Cl.
CPC .................. *A61K 8/19* (2013.01); *A61K 8/26* (2013.01); *A61K 8/29* (2013.01); *A61K 8/676* (2013.01); *A61K 8/678* (2013.01); *A61K 8/97* (2013.01); *A61Q 17/04* (2013.01); *A61K 2800/522* (2013.01)

(58) Field of Classification Search
None
See application file for complete search history.

(56) References Cited

U.S. PATENT DOCUMENTS

2010/0166687 A1   7/2010   Golz-Berner et al.

FOREIGN PATENT DOCUMENTS

| CN | 1306419 | 8/2001 |
|---|---|---|
| CN | 103813776 | 5/2014 |
| DE | 102007010861 | 9/2008 |
| EP | 1591104 | 11/2005 |
| EP | 2233127 | 9/2010 |
| EP | 2731580 | 9/2016 |
| WO | 2004105706 | 12/2004 |
| WO | 2008104607 | 6/2009 |

OTHER PUBLICATIONS

"Firming & Comforting Radiant Tan Body Cream SPF 30", Mintel (May 2011) Database accession No. 1545688.
International Search Report and the Written Opinion of the ISA dated Nov. 11, 2013 in PCT Application No. PCT/EP2012/063839. (10 pages).
Muizzuddin, et al., "Effect of antioxidants and free radical scavengers on protection of human skin against UVB, UVA and IR irradiation", Skin Research and Technology (1999) 5: 260-265.
Korean Application Serial No. 10-2014-7003659, Final Office Action dated Sep. 26, 2016, 3 pgs.

*Primary Examiner* — David J Blanchard
*Assistant Examiner* — Sarah Chickos
(74) *Attorney, Agent, or Firm* — Schwegman Lundberg & Woessner, P.A.

(57) ABSTRACT

The disclosure relates to a cosmetic composition for use in protecting the human skin against infrared (IR) radiation. The cosmetic composition includes a first plant extract mixture of Green Coffee Seed Extract, *Camellia Sinensis* Leaf Extract, *Pongamia Pinnata* Seed Extract, *Angelica Archangelica* Root Extract and *Citrus Aurantium* (Bitter Orange) Peel extract; a second mixture of vitamins E and C and derivatives thereof; a third mixture of particular materials of ruby powder, mica and titanium dioxide, the ruby powder having a particle size of $d_{90}<10$ μm; and cosmetic auxiliaries. The composition shows a synergistic effect because of a significantly higher degree of protection than the single groups of substances.

11 Claims, No Drawings

USE OF COSMETICS AGAINST INFRARED RADIATION

CROSS REFERENCE TO RELATED APPLICATIONS

This application is a § 371 national stage entry of International Application No. PCT/EP2012/063839, filed on Jul. 13, 2012 and entitled "USE OF COSMETICS AGAINST INFRARED RADIATION", which claims priority to European Application No. 11173973.6, filed on Jul. 14, 2011, the entireties of which are incorporated herein by reference.

The invention refers to a cosmetic composition for use in protecting the human skin against infrared (IR) radiation.

The effect of antioxidants against UVB, UVA and IR irradiation was described in Skin Research and Technology 1999, 5, 260-265 by use of Vitamin E linoleate, butylated hydroxytoluene, nordihydroguanidinic acid and Mg-ascorbyl phosphate.

From WO 2008/104607 a cosmetic light-protective agent is known comprising UVA and UVB filters, Sea Buckthorn oil, a powder of glass or a precious stone such as ruby and an infra-red absorbing glass.

EP 2233127 A1 describes a pharmaceutical composition with antioxidants for protecting the skin against damages by infrared radiation, wherein the damage is caused by activation of the development of matrix metallo proteinase-1.

The aim of the invention is to develop a cosmetic composition for the use against IR radiation with improved effect against free radicals which radicals will be produced under IR radiation in the uncovered human skin. A further aim is to clearly decrease the amounts of the IR-effective substances to a very low level.

The invention is characterised by the use of a main mixture for preparing a composition for protecting the skin against infrared radiation, wherein the main mixture comprises a first plant extract mixture of
Green Coffee Seed Extract,
*Camellia Sinensis* Leaf Extract,
*Pongamia Pinnata* Seed Extract,
*Angelica Archangelica* Root Extract and
*Citrus Aurantium* (Bitter Orange) Peel extract;
a second mixture of vitamins E and C and derivatives thereof;
a third mixture of particular materials of
ruby powder, mica and titanium dioxide with a particle size in the range of 3-10 µm;
and cosmetic auxiliaries for the final composition.

That means, according to the invention the cosmetic composition for use in protecting the skin against IR radiation comprises
a first mixture of plant extracts of Green Coffee Seed Extract, *Camellia Sinensis* Leaf Extract, *Pongamia Pinnata* Seed Extract, *Angelica Archangelica* Root Extract and *Citrus Aurantium* (Bitter Orange) Peel extract,
a second mixture of vitamins E (tocopherol) and C (ascorbic acid) and derivatives of the vitamins;
a third mixture of particular materials of ruby powder, mica and titanium dioxide, all particular materials with a particle size in the range of 3-10 µm;
and cosmetic auxiliaries, wherein the auxiliaries do not comprise IR protecting and IR absorbing ingredients. The cosmetic composition of the present invention which is intended for use in protecting the skin against IR radiation does especially not comprise IR absorbing glasses and sea Buckhorn oil which has also been found to be an IR protecting ingredient.

The plant extract mixture of the cosmetic composition includes preferably extracts from green coffee beans, from leaves of green tea (*Camellia sinensis*), from seeds of *Pongamia pinnata*, from roots of *Angelica archangelica* and from peel of *Citrus aurantium* (Bitter orange). The extracts are prepared by extraction with a monovalent or multivalent alcohol or a mixture of such alcohol(s) with water at room temperature (about 15-30° C.). The extracts are used in liquid or dried form. An especially preferred plant extract mixture is a mixture of liposomic encapsulated plant extracts of 1-4% *Camellia Sinensis* Leaf Extract, 1-4% Green Coffee Seed Extract, 1-4% *Pongamia Pinnata* Seed Extract, 1-4% *Angelica Archangelica* Root Extract, 1-4% *Citrus Aurantium* Peel Extract, 2-10% phospholipids in an aqueous-alcoholic suspension wherein the alcohol content is in the range of 4-12%, wherein all concentrations are related to the weight of the plant extract mixture.

The amount of each of the used plant extracts is in the range of 0.0001 to 0.05% by weight, preferably 0.001 to 0.005% by weight of dry mass of plant extract and related to the total weight of the cosmetic composition. A preferred range of all plant extracts together is 0.008 to 0.9, more preferred 0.008 to 0.05, especially 0.008% by weight, and most preferred no more than 0.009% by weight, related to the total weight of the cosmetic composition.

The second mixture of the cosmetic composition of the invention comprises vitamins E (tocopherol) and C (ascorbic acid) and derivatives of the vitamins. Preferred vitamin derivatives of vitamin C are ascorbyl acetate, ascorbyl phosphate, ascorbyl palmitate or magnesium ascorbyl phosphate or mixtures thereof, preferably ascorbyl palmitate. Preferred vitamin derivatives of vitamin E are α-tocopherol, tocopheryl acetate, tocotrienols, marine derived tocopherol or mixtures thereof.

An especially preferred second mixture of the cosmetic composition of the invention is PEG-8 & Tocopherol & Ascorbyl palmitate & Ascorbic acid & Citric acid (trade name: Oxynex K).

The range of all vitamins and vitamin derivatives added to the composition is 0.0003 to 0.02, preferably 0.0003 to 0.005% by weight, related to the total weight of the composition.

The third mixture as a part of the main mixture of the invention contains ruby powder (trade name: Rubisa), mica and titanium dioxide (trade name: Timiron Starluster MP-115).

Ruby is a known precious stone on the chemical basis of alumina. Ruby has a rhomboedric or trigonal crystalline system and is used in a micronized powder form with particle sizes of $d_{90}<10$ µm, preferably $d_{90}=3$ to 8 µm.

Mica is a sheet silicate with differently coordinated cations and dioctaedric or trioctaedric crystalline systems. Common micas are Muscovite, Phlogopite, Biotite etc. Mica is a product also known in the cosmetic field, especially used for glitter effects.

Titanium dioxide is a known cosmetic material used for whitening effects, as UV light absorber and colorant.

Concentration ranges of the particular materials are 0.05 to 10%, preferably 0.05 to 8%, especially 0.05 to 1.0%, specially preferred 0.05 to 0.4% ruby powder,
0.05 to 0.4%, preferably 0.05 to 0.2% mica,
0.05 to 10%, preferably 0.05 to 5%, especially 0.05 to 0.4% titanium dioxide,
all are % by weight and related to the total weight of the cosmetic composition.

The inventors found that a cosmetic composition comprising a first plant extract mixture of Green Coffee Seed Extract, *Camellia Sinensis* Leaf Extract, *Pongamia Pinnata* Seed Extract, *Angelica Archangelica* Root Extract and *Citrus Aurantium* (Bitter Orange) Peel extract; a second mixture of vitamins E and C and derivatives thereof; a third mixture of particular materials of ruby powder, mica and titanium dioxide with a particle size in the range of 3-10 µm; and cosmetic auxiliaries for the final composition have a synergistic effect in the protection of the human skin from IR-induced free radicals, wherein the composition does only contain the mentioned IR protecting ingredients.

The range of near-infrared radiation, which is problematical for human skin, is about 780-1.400 nm. Partly artificial lamps range up to 1,600 nm. The protection by such antioxidants as superoxide dismutase or glutathione reductase, which are inherently present in the skin to protect it against free radicals, is not sufficient in long-term actinic exposure. It was found that the plant extracts of the first mixture alone, vitamins alone and the particular materials alone provide a certain protection against free radicals induced by IR radiation. Surprisingly, however, a mixture of these special substances in a single composition shows a significantly higher degree of protection of nearly 100% more than the sum of the protection in percents provided by the individual groups of substances. The results are represented in the Comparison Test.

It was additionally found in consumer tests, e.g. with an oil free spray SPF 15, that in over 90% it helps to prevent an overheating sensation, limits redness risks and limits irritation risks nearly to the same limit.

In comparison with products on the market the composition of the invention shows clearly improved anti-aging effects, better cell protection from IR and generally better IR protection.

Cosmetic auxiliaries which may be contained in the composition are e.g. inorganic and organic sunscreens (UV filters), emulsifying agents, pigments, preservatives, gel formers, dyes, perfumes, stabilisers, film-forming agents, emollients, conditioning agents, moisturizing substances, chelating agents, SPF boosters, humectants, anti-inflammatory natural active agents, pH regulators or mixtures thereof, but no IR protecting or IR absorbing ingredients.

Especially preferred are one or more of UV filters, emulsifying agents, moisturizing substances, gel formers, SPF boosters, emollients, silicone oils, emulsion stabilisers, pH regulators or preservatives.

Additional dermatological or cosmetic auxiliaries which can be used in the composition include e.g. water, vitamins, enzymes, other plant extracts, polymers, phospholipids, panthenol, allantoin, synthetic ethers and esters, fatty acids, monovalent and multivalent alcohols, silicones, minerals, oils especially plant oils, waxes, biotechnological extracts. Biotechnological extracts are e.g. CLR Repair Complex or Yeast Complex B (both of CLR, Chem. Lab. Dr. Kurt Richter GmbH, Berlin, Germany); Stimulhyal, Primalhyal 50 or 300 (all of SOLIANCE, Paris, France).

Especially preferred are water, other plant extracts or mixtures of extracts with the provision that they are no IR protecting ingredients, synthetic polymers, esters, ethers, fatty acids, monovalent and multivalent alcohols, silicones, silicates, waxes.

The cosmetic composition of the invention can be formulated as different cosmetic products by adding the corresponding ingredients common for such products such as e.g. lotions, oils, creams, day creams, night creams, day care products with UV protection, gels, masks, balms, powders, eye-liftings, tan glows, tinted creams, fillers, tissue masks, pre-sun products, sun products, after-sun products, self-tans, make-ups, compact powders, photo protecting products, sprays, makeup-removers, cleansers, target products, primers, blush powders, bath products such as shower and bath gels or salts, lipsticks or deo sticks.

Emulsion products include multiple emulsions, micro emulsions and nano emulsions in the form of W/O, O/W, W/Si, Si/W, W/O/W, O/W/O, O/W/Si and W/Si/W emulsions (O=Oil, W=Water, Si=Silicone). Other products such as anhydrous systems like Si/O are also included.

Pre-sun products are e.g. pre-sun gels, pre-sun lotions, pre-sun creams or pre-sun oils. Sun products are gels, creams, lotions, oils, sprays or daily protective skin care products with different Sun Protection Factors (SPF) in the range from SPF 2 to SPF 50, e.g. SPF 6, SPF 10, SPF 15, SPF 20, SPF 25, SPF 30, SPF 50 and SPF 50+. The different SPFs are dependent on the kind and amount of UV filter substances.

Suitable cosmetic gel-forming agents for the preparation of a gel are e.g. carbomer, xanthan gum, carrageenan, acacia gum, guar gum, agar-agar, alginates and tyloses, magnesium aluminium silicates, carboxymethyl cellulose, hydroxyethyl cellulose, quaternized cellulose, quaternized guar, certain polyacrylates, such as acrylates/C10-30 alkyl acrylate cross polymer, polyvinyl alcohol, polyvinylpyrrolidone.

Especially preferred are according to the invention xanthan gum, Carbomer, Ammonium Acryloyldimethyltaurate/ VP Copolymer Ammonium Acryloyldimethyltaurate/Beheneth-25 Methacrylate Crosspolymer Acrylates/C12-22 Alkyl Methacrylate Copolymer, Magnesium Aluminium Silicate, Sodium Acrylate/Sodium Acryloyldimethyl Taurate Copolymer, Hydroxyethyl Acrylate/Sodium Acryloyl Dimethyl Taurate Copolymer, Polyester-5 and Acrylates/Vinyl Neodeconoate Crosspolymer, Sodium Polyacrylate or Polyacrylamide/C13-14 Isoparaffin/Laureth 7/Styrene/Acrylate Copolymer Sodium Lauryl Sulfate or mixtures thereof.

For the preparation of sun products it is moreover advantageous to include into a cosmetic product of the invention together with the inventive ingredients corresponding water and/or oil soluble UVA or UVB filters or both. Advantageous oil-soluble UVB filters include 4-amino benzoic acid derivatives such as e.g. 4-(dimethylamino)-benzoic acid-(2-ethylhexyl) ester; esters of cinnamic acid such as e.g. 4-methoxy cinnamic acid (2-ethylhexyl) ester, benzophenone derivatives such as e.g. 2-hydroxy-4-methoxy benzophenone or mixtures thereof.

Preferred oil-soluble UV filters are Butyl-Methoxybenzoylmethane, Ethylhexyl Methoxycinnamate, Ethylhexyl Salicylate, and/or Bis-Ethyl Hexyl Phenol Methoxyphenyl Triazine.

Water-soluble UVB filters are, for example, sulfonic acid derivatives of benzophenone or of 3-benzylidene camphor or salts, such as Na or K salts, of 2-phenyl benzimidazole-5-sulfonic acid. UVA filters which may be contained in the cosmetic composition of the present invention include dibenzoyl methane derivatives such as Butyl-Methoxybenzoylmethane.

Especially preferred are Butyl Methoxydibenzoylmethane, Ethylhexyl Methoxycinnamate, Ethylhexyl Salicylate, Octocrylene, Ethylhexyl Methoxycinnamate, isoamyl-p-Methoxycinnamate, Ethylhexyltriazone, Diethylhexyl Butamido Triazone, Methylene Bis-Benzotriazolyl Tetramethylbutylphenol, Disodium Phenyl Dibenzimidazole Tetrasulfonate, Bis-Ethylhexyloxyphenol Methoxyphenyl Triazine and/or Benzophenone-3. Inorganic pigments as sunscreen filters are metal oxides such as $TiO_2$, $SiO_2$, $Fe_2O_3$, $ZrO_2$, MnO, $Al_2O_3$, which can also be used in mixtures thereof.

The cosmetic composition of the present invention can also comprise tanning agents. Such tanning agents are e.g. isatin, glycerine aldehyde, meso-tartaric acid aldehyde, glutaraldehyde, erythrulose, pirazoline-4,5-dion derivatives, dihydroxyacetone (DHA) and/or 4,4-dihydroxy pirazoline-5-dion derivatives.

Compositions of the invention can also comprise humectants such as glycerine, butylene glycol, propylene glycol and mixtures thereof.

Compositions of the invention can also comprise moisturising, pores tightening or firming agents, mostly from plants and algae, e.g. hazel water, *Pisum Sativum* (Pea) Extract.

Further ingredients of the composition of the present invention are oils, emulsifiers, esters and pigments.

Oils used for the invention can be usual cosmetic oils such as e.g. mineral oil, hydrogenated polyisobutene, squalane from synthetic or natural sources, saturated or unsaturated vegetable oils, or mixtures of two or more thereof.

Especially suitable oils are, for example, silicone oils, mineral oils, hydrogenated polyisobutene, polyisoprene, squalane, tridecyltrimellitate, trimethylpropane triisostearate, isodecylcitrate, neopentyl glycol diheptanoate, PPG-15-stearyl ether, calendula oil, jojoba oil, avocado oil, macadamia nut oil, castor oil, cocoa butter, Inca inchi oil, coconut oil, corn oil, cotton seed oil, olive oil, palm kernel oil, rapeseed oil, safflower seed oil, sesame seed oil, soybean oil, sunflower seed oil, wheat germ oil, grape kernel oil, kukui nut oil, buriti oil, calendula oil, thistle oil and mixtures thereof.

Depending upon the oils selected, the cosmetic properties of a solid composition of the invention such as softness, hardness or spreading effects can be affected.

Esters used in the composition of the present invention ban be esters of polyols, suitable esters of polyols are esters of $C_{10}$-$C_{15}$ fatty acids and alcohols, esters of $C_{10}$-$C_{15}$ fatty acids and glycols, or esters of hydroxy fatty acids. Branched $C_{12}$-$C_{15}$ alkyl esters in conjunction with other esters such as di- or tri-esters of polyols are particularly advantageous in the oil phase, with esters of linear-chain alcohols and branched acids being particularly favourable. All these suitable esters are derived from primary alcohols. Preferred esters are Dicaprylyl Carbonate/Decyl Cocoate, Diisopropyl Sebacate/Dibutyl Adipate and Isopropyl Palmitate.

According to the invention suitable substances for the oil phase include Isohexadecane, PEG-40-Stearate, Sorbitan Tristearate, Behenyl Alcohol, Neopentyl Glycol Diheptanoate, Propylene Glycol Dicaprylate, Dioctyl Adipate, Cocoa-caprylate/Caprate, Diethylhexal Adipate, Diisopropyl Dimer Dilinoleate, Diisostearyl Dimer Dilinoleate, Isohexadecane, *Butyrospermum Parkii* (shea) Butter, $C_{12-13}$ Alkyl Lactate, Di-$C_{12-13}$ Alkyl Tartrate, Tri-$C_{12-13}$ Alkyl citrate, $C_{12-15}$ Alkyl Lactate, PPG Dioctanoate, Diethylene Glycol Dioctanoate, Meadowfoam Oil, Babassu Oil, Jojoba Oil, Rice Oil, $C_{12-15}$ Alkyl Oleate, Avocado Oil, Tridecyl Neopentanoate, Beeswax, Betearyl Alcohol and Polysorbate 60, $C_{18-26}$ Triglycerides, Cetearyl Alcohol & Cetearyl Glucoside, Acetylated Lanolin, VP/Eicosene Copolymer, Glyceryl Hydroxystearate, $C_{18-36}$ Acid Glycol Ester, with substances such as $C_{18-36}$ Triglycerides, Caprylic/Capric Triglyceride, Glyceryl Hydroxystearate and mixtures thereof. Also suitable and preferred are Cetyl Alcohol & Glyceryl Stearate & PEG 75 Stearate & Ceteth-20 & Steareth-20, Lauryl Glucoside & Polyglyceryl-2 Dipolyhydroxystearate, Behenth-25, Polyamide-3 & Pentaerythrityl Tetra-Di-T-Butyl Hydroxycinnamate, Polyamide-4, PEG-100 Stearate, Potassium Cetylphosphate, Stearic Acid or Hectorites or mixtures of two or more thereof.

Cosmetic compositions according to the invention may preferably exist as O/W or W/O emulsions as well as emulsion from the above-mentioned type of multiple, micro or nano emulsions. Suitable emulsifiers for O/W emulsions are for instance addition products of 2-30 mol ethylene oxide to linear $C_8$-$C_{22}$ fatty alcohols, to $C_{12}$-$C_{22}$ fatty acids and to $C_8$-$C_{15}$ alkylphenols; $C_{12}$-$C_{22}$ fatty acid monoesters and diesters of addition products of 1-30 mol ethylene oxide to glycerine; glycerine monoesters and diesters as well as sorbitan monoester and diester of $C_6$-$C_{22}$ fatty acids, polyol- and polyglycerine ester; addition products of ethylene oxide to castor oil; as well as ampholytic tensides.

Suitable emulsifiers for W/O emulsions are for instance addition products of 2-15 mol ethylene oxide to castor oil, esters of $C_{12}$-$C_{22}$ fatty acids and glycerine, polyglycerine, glycols, pentaerythrite, sugar alcohols (e.g. sorbite), polyglucosides (e.g. cellulose), polyalkylene glycols, wool alcohols, copolymers of polysiloxan polyalkyl polyether.

Suitable emulsifiers for multiple emulsions and micro emulsions are for instance Tribehenin PEG-20 Esters, PEG-12 Dimethicone Crosspolymer, Lauryl PEG/PPG-18/18 Methicone, PEG-PPG-19/19 Dimethicone including Cyclopentasiloxane, Polyglyceryl-6 Dioleate and PEG-8 Caprylic/Capric Glycerides.

The cosmetic composition of the invention may also comprise pigments, pigment mixtures or powders with a pigment-like effect, also including those with a pearl-gloss effect. They may include, for example, iron oxides, aluminium silicates such as ochre, titanium dioxide, kaolin, manganese containing clays, silicium dioxide, zinc oxide, calcium carbonate, French chalk, nylon beads, ceramic beads, expanded and non-expanded synthetic polymer powders, powdery natural organic compounds such as milled solid algae, milled plant parts, encapsulated and non-encapsulated cereal starches.

Further cosmetic auxiliaries which may be comprised by the cosmetic composition of the invention are waxes. The waxes may be selected among natural plant waxes, animal waxes, natural and synthetic mineral waxes and synthetic waxes. The composition may include carnauba wax, candelilla wax, ozokerite, beeswax, montan wax, wool wax, ceresine, micro waxes, paraffin waxes, petrolatum, silicon wax, polyethylene glycol waxes or polyethylene glycolester waxes or mixtures thereof.

A further object of the invention is a cosmetic composition for use in protecting the skin against IR radiation, wherein the composition comprises 0.05-1.0%, preferably 0.05-0.9% by weight of a mixture of plant extracts and vitamins E and C and derivatives of the vitamins;

particular materials of 0.05-1.0%, by weight ruby powder, 0.05-0.4% by weight mica and 0.05-10.0%, preferably 0.05-5.0% by weight titanium dioxide, all particular materials with a particle size in the range of 3-10 μm;

and further cosmetic auxiliaries up to a total amount of 100% of the composition, wherein the auxiliaries do not comprise IR protecting or IR absorbing ingredients.

The mixture of plant extracts is a mixture of Green Coffee Seed Extract, *Camellia Sinensis* Leaf Extract, *Pongamia Pinnata* Seed Extract, *Angelica Archangelica* Root Extract and *Citrus Aurantium* (Bitter Orange) Peel Extract.

A further object of the invention is a method for protecting the skin against IR radiation which comprises the application onto the human skin of a cosmetic composition comprising 0.05-1.0% by weight of a mixture of plant extracts of Green Coffee Seed Extract, *Camellia Sinensis* Leaf Extract, *Pongamia Pinnata* Seed Extract, *Angelica Archangelica* Root Extract and *Citrus Aurantium* (Bitter Orange) Peel extract and vitamins E and C and derivatives of the vitamins; particular materials of 0.05-1.0%, preferably 0.05-0.9% by weight ruby powder, 0.05-0.4% by weight mica and 0.05-10.0%, preferably 0.05-5.0% by weight titanium dioxide, all particular materials with a particle size in the range of 3-10 µm; and further cosmetic auxiliaries up to a total amount of 100% of the composition, wherein the cosmetic auxiliaries do not comprise IR protecting or IR absorbing ingredients.

The invention shall now be described in detail for the cosmetic composition of the invention by examples. All figures given as percentages are % by weight, if not specified otherwise. In the following examples basically INCI-names of the ingredients are used.

EXAMPLE 1-3 EMULSIONS SPF 25-30

|  | Ex. 1 | Ex. 2 | Ex. 3 |
|---|---|---|---|
| Phase A |  |  |  |
| Ethylhexyl Palmitate | 3.7 | 3.7 | 3.7 |
| C12-15 Alkyl Benzoate | 7.9 | 7.9 | 7.9 |
| Isopropyl Palmitate | 3.0 | 3.0 | 3.0 |
| TiO$_2$ & Al(OH)$_3$ & Stearic Acid | 0.5 | 1.5 | 2.7 |
| Butyl Methoxydibenzoyl Methane | 3.0 | 3.0 | 3.0 |
| Bis-Ethylhexyloxyphenol Methoxyphenyl Triazine | 2.0 | 2.0 | 2.0 |
| Octocrylene | 1.5 | 1.5 | 1.5 |
| Diethylhexyl Butamide Triazone | 1.0 | 1.0 | 1.0 |
| Stearic Acid | 2.1 | 2.1 | 2.1 |
| Tribehenin PEG-20 Esters | 2.9 | 2.9 | 2.9 |
| Phase B |  |  |  |
| Water | q.s. ad 100 | q.s. ad 100 | q.s. ad 100 |
| Disodium EDTA | 0.05 | 0.05 | 0.05 |
| Glycerine | 7.5 | 7.5 | 7.5 |
| Propylene Glycol | 1.5 | 1.5 | 1.5 |
| Potassium Cetyl Phosphate | 0.5 | 0.5 | 0.5 |
| Chlorphenesin | 0.2 | 0.2 | 0.2 |
| Ruby Powder (Trade name: Rubisa) | 0.05 | 0.15 | 0.25 |
| Mica & TiO$_2$ (Trade name: Timiron Starluster MP-115) | 0.15 | 0.35 | 0.4 |
| Hydroxypropyl Methylcellulose | 0.35 | 0.35 | 0.35 |
| Acrylates/C10-30 Alkyl Acrylate Crosspolymer | 0.21 | 0.21 | 0.21 |
| Phase C |  |  |  |
| Cyclopentasiloxane | 8.0 | 8.0 | 8.0 |
| Phenoxyethanol | 0.7 | 0.7 | 0.7 |
| Phase D |  |  |  |
| RPF Complex * | 0.05 | 0.19 | 0.3 |
| Mixture of vitamins E & C incl. derivatives thereof (Trade name: Oxynex K) | 0.025 | 0.04 | 0.2 |
| Triethanolamine | 0.25 | 0.25 | 0.25 |
| Perfume | 0.4 | 0.4 | 0.4 |
| Alcohol & Water | 2.0 | 2.0 | 2.0 |

* RPF Complex: Green Coffee Seed Extract (2%), Camellia Sinensis Leaf Extract (2%), Pongamia Pinnata Seed Extract (2%), Angelica Archangelica Root Extract (2%), Citrus Aurantium Peel Extract (1%), all in wt-% related to the weight of the RPF complex mixture and encapsulated in lecithin liposomes and also comprising 5 to 10% by weight of an alcohol, and water and auxiliaries.

Phases A and B are separately heated up while stirring till 75-80° C. Phase A is dispersed in phase B till homogeneity of the emulsion. The mixture is cooled down to 50-55° C. while stirring. Phase C is added to the mixture till homogeneity and the total mass is cooled to <30° C. Finally the ingredients of Phase D are added while stirring. The emulsion is homogenised.

EXAMPLE 4 COMPARATIVE TEST 1

The protection from IR induced free radicals is stated by tests on skin biopsies.

Human skin samples were obtained from surgery from healthy subjects. Skin flaps (about 1×1 cm) were washed with an isotonic NaCl solution. Adhered subcutis and fascia were removed. The epidermal/dermal skin sheet was kept on filters and on ice. Scavenging and accumulating of free radicals generated by IR radiation were realized by the spin trap PBN (Phenyl-tert-butylnitrone). The skin biopsies incubated for 10 min in the spin trap solution before irradiation.

Different substance mixtures were applied to the skin surface of the skin flaps with an amount of 2 mg/cm$^2$ followed by a storage of 15 min in the dark at room temperature before IR radiation. A punch biopsy (diameter 6 mm, thickness about 1 mm) was extracted from the skin flap and positioned in the sample holder. The sample holder was used for IR radiation and Electron Spin Resonance (ESR) measurement. The measurement was performed immediately after IR radiation.

The used ESR X-band spectrometer was an ERS 300 (ZWG, Germany) with the following spectrometer settings: microwave frequency 9.52 GHz, microwave power 20 mW, modulation frequency 100 kHz, modulation amplitude 0.2 mT, magnetic field scan 20 mT. The IR exposure of the skin biopsies was carried out with an IR lamp SOLLUX 500, Germany, emitting a continuous spectrum in the IR range (700 nm to 1600 nm, with a very homogeneous beam over the surface. The skin biopsies were irradiated for 800 sec. Substance Groups Measured:

A: Base formula *[1]
B: Base formula + particular materials
   (2.07% TiO$_2$ + 0.18% Mica + 0.1% Ruby Powder)
C: Base formula + plant extracts*[2] + vitamins
   (First mixture plant extracts 0.1% + second mixture vitamins*[3] 0.05 %)
D: Base formula of Group A + Particular materials of Group B (same concentrations) + Plant extracts and vitamins of Group C (same concentrations)

| *[1] The base formula refers to the following composition | % |
|---|---|
| Emollients Ethylhexyl Palmitate & C12-15 Alkyl Benzoate & Isopropyl Palmitate | 13.0 |
| UV Filters Butyl Methoxydibenzoylmethane & Ethylhexyl Methoxycinnamate & Bis-Ethylhexyloxyphenol Methoxyphenyl Triazine & Octocrylene & Diethylhexyl Butamido Triazone | 10.0 |
| Emulsifying agents Stearic Acid & Tribehenin PEG-20 Esters & Potassium Cetyl Phosphate | 5.6 |
| Water | q.s. ad 100 |
| Disodium EDTA | 0.05 |
| Humectants Glycerine & Propylene Glycol | 7.0 |
| Viscosity-increasing agents Hydroxypropyl Methylcellulose & Acrylates/Cl 0-30 Alkyl Acrylate Crosspolymer | 0.5 |
| Emollients Cyclopentasiloxane & Dimethiconol | 7.8 |
| Triethanolamine | 0.3 |
| Preservatives Chlorphenesin & Phenoxyethanol | 0.9 |

*[2]Plant extracts: Green Coffee Seed Extract, Camellia Sinensis leaf Extract, Pongamia Pinnata Seed Extract, Angelica Archangelica Root Extract, Citrus Aurantium Peel Extract
*[3]Vitamins: vitamin C, vitamin E, ascorbyl palmitate The protection (in %) of the substance groups measured is calculated by comparing the quantity of free radicals in protected and non protected skin. The results are:

Group A: 0.0% protection
Group B: 2.6% protection
Group C: 9.1% protection
Group D: 22.7% protection.

The result shows nearly twice enhanced percents for Group D in comparison with the sum of Groups A+B+C (11.7%). This is a clear synergistic effect.

EXAMPLE 5 COMPARATIVE TEST 2

A further comparison was made between a sun lotion of the invention with SPF 30 and a product of the market with a special IR-A protection complex (Ladival® SPF 30 for kids).

The measuring protocol was the same as in Example 4. The results are

Product of the market 33% protection
Product of the invention: 62% protection.

This result underlines the synergistic effect presented in Example 4.

The invention claimed is:

1. A method for preparation of a cosmetic composition for protecting the skin against IR radiation, the cosmetic composition consisting of:
   0.05-1.0 by weight of a mixture of plant extracts of Green Coffee Seed Extract, *Camellia Sinensis* Leaf Extract, Pongamia *Pinnata* Seed Extract, *Angelica Archangelica* Root Extract and *Citrus Aurantium* (Bitter Orange) Peel extract and vitamins E and C and derivatives of the vitamins;
   a mixture of particulate materials of 0.05-1% by weight ruby powder, 0.05-0.4% by weight mica and 0.05-10.0% by weight titanium dioxide, wherein ruby powder has a particle size of $d_{90}$<10 pm;
   and cosmetic auxiliaries up to a total amount of 100% of the composition, wherein the cosmetic auxiliaries do not comprise IR protecting ingredients;
   wherein the method comprises the steps of:
   a) preparing the mixture of plant extracts,
   b) adding the mixture of particulate materials; and
   c) adding the cosmetic auxiliaries.

2. The method according to claim 1, wherein the amount of all plant extracts in the cosmetic composition together is 0.008 to 0.9% by weight.

3. The method according to claim 1, wherein the amount of all plant extracts in the cosmetic composition together is 0.008 to 0.05% by weight.

4. The method according to claim 1, wherein the amount of all plant extracts in the cosmetic composition is no more than 0.009% by weight.

5. The method according to claim 1, wherein the amount of each of the plant extracts in the plant extract mixture is in the range 0.001 to 0.005% by weight of dry mass of plant extract and related to the total weight of the cosmetic composition.

6. The method according to claim 1, wherein the amount of each of the plant extracts in the plant extract mixture is in the range of 0.0001 to 0.05% by weight of dry mass of plant extract and related to the total weight of the cosmetic composition.

7. The method according to claim 1, wherein the vitamin derivatives are ascorbyl acetate, ascorbyl phosphate, ascorbyl palmitate or magnesium ascorbyl phosphate or mixtures thereof.

8. The method according to claim 1, wherein the vitamin derivative is ascorbyl palmitate.

9. The method according to claim 1, wherein the total amount of all vitamins and vitamin derivatives within the composition is 0.0003 to 0.02% by weight, related to the total weight of the composition.

10. The method according to claim 1, wherein the total amount of all vitamins and vitamin derivatives within the composition is 0.0003 to 0.005% by weight, related to the total weight of the composition.

11. A method for protecting the skin against IR radiation which comprises the application onto the human skin of a cosmetic composition prepared according to claim 1.

* * * * *